United States Patent [19]
Tamura et al.

[11] 3,980,433
[45] Sept. 14, 1976

[54] METHOD FOR DETERMINING CARBOXYLIC ACID AND SYSTEM FOR CARRYING OUT THE METHOD

[76] Inventors: Zenzo Tamura, 17-11, Sanno 2-Chome, Ota, Tokyo; Takenori Tanimura, 8-11, Matsunoki-cho 1-chome, Suginami, Tokyo; Yasuhiko Kasai, 24-303, Keyakidaidanchi, 13-2, Wakaba-cho 1-chome, Tachikawa, Tokyo, all of Japan

[22] Filed: Oct. 15, 1974

[21] Appl. No.: 514,942

[30] Foreign Application Priority Data
Oct. 17, 1973  Japan............................ 48-115712
Mar. 8, 1974  Japan............................ 49-26209
Mar. 12, 1974  Japan............................ 49-27756

[52] U.S. Cl. .................... 23/230 M; 23/230 R; 23/253 R
[51] Int. Cl.² ................. G01N 33/16; G01N 21/24; G01N 33/02
[58] Field of Search ............. 23/230 R, 230 M, 253

[56] References Cited
UNITED STATES PATENTS 3,341,299  9/1967  Catravas ........................... 23/253 X
3,728,079  4/1973  Moran ................................ 23/253
3,883,305  5/1975  Hoskins et al. ...................... 23/253

OTHER PUBLICATIONS

Goldenberg et al., "Colorimetric Determination of Carboxylic Acid Derivatives as Hydroxamic Acids," Anal. Chem. vol. 30, No. 8, Aug. 1958 pp. 1327–1330.

Connors et al., "Detection and Determination of Some Carboxylic Acids in Aqueous Solution by Ni(II)–Catalyzed Hydroxamic Acid Formation," Anal. Chem. vol. 44, No. 2 Feb. 1972 pp. 336–339.

*Primary Examiner*—R.E. Serwin
*Attorney, Agent, or Firm*—Ostrolenk, Faber, Gerb & Soffen

[57] ABSTRACT

A method for determining the amount of carboxylic acid in which a carboxylic acid in a sample sample is reacted with a hydroxylammonium salt under the presence of carbodiimide to provide hydroxamic acid and the thus formed hydroxamic acid is reacted with a ferric compound to provide ferric hydroxamate, and a system for carrying out the method are disclosed.

10 Claims, 1 Drawing Figure

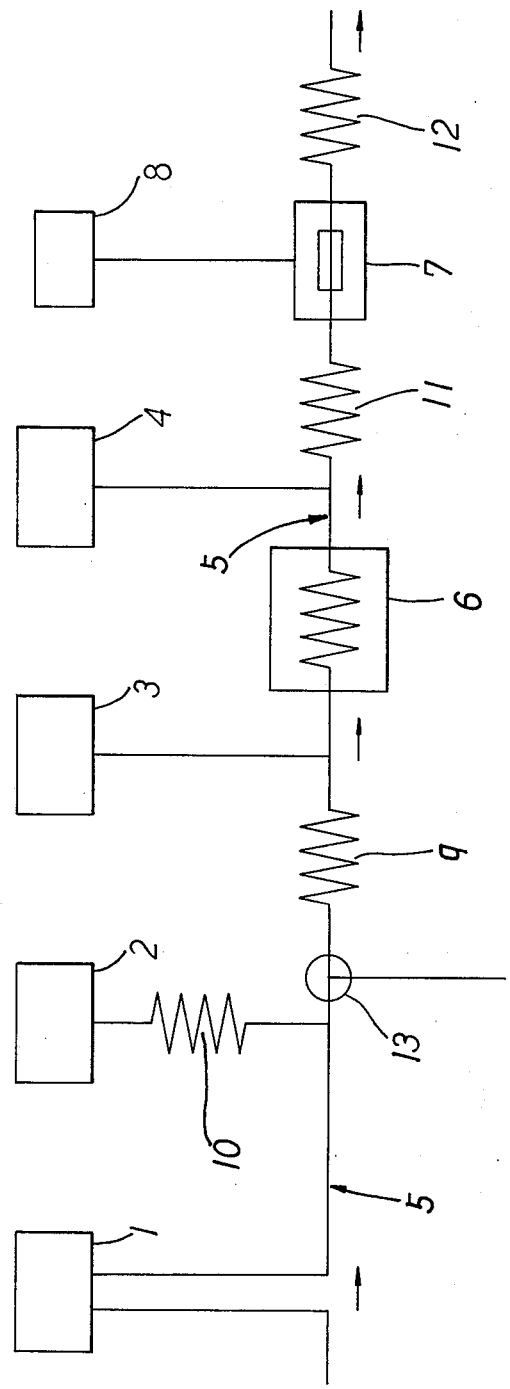

METHOD FOR DETERMINING CARBOXYLIC ACID AND SYSTEM FOR CARRYING OUT THE METHOD

BACKGROUND OF THE INVENTION

This invention relates to a method for determining carboxylic acid and a system for carrying out the method.

At present, it has been attempted to improve and control the quality of various food products containing carboxylic acid based on the results of determination of the amount of the carboxylic acid contained in the materials or semiprocessed foods present in the processing stages of the production of the food products or determine the quality of the food products by detecting the amount of carboxylic acid contained in the final food products. In the field of clinical medicine, any abnormal condition or disease of a living body is diagnosed by detecting or determining the value of carboxylic acid within the living body and then comparing the detected value of carboxylic acid with a predetermined normal value of carboxylic acid. In this way, the carboxylic acid determination is considered important in various fields.

Determination of carboxylic acid has been conventionally conducted by (1) preparing an active derivative of carboxylic acid such as carboxylic acid chloride, carboxylic acid ester or carboxylic acid anhydride, for example, causing the derivative to react with hydroxylamine to form hydroxamic acid, causing the hydroxamic acid to react with triferric ion to form ferric hydroxamate and finally, directly observing the color development of the ferric hydroxamate or determining the absorptivity of the ferric hydroxamate in a known procedure, (2) by determining variations in the color development of carboxylic acid through the addition of a pH indicator to the carboxylic acid, (3) by causing carboxylic acid to react with an oxidization reagent and then determining the consumed amount of the reagent or the amount of the reaction product or (4) by determining variations in the pH of the carboxylic acid by a pH meter.

Out of the various prior art methods for determination of carboxylic acid referred to above, method (1) is the most commonly practiced method, but if water is present in the formation of an active derivative from carboxylic acid such as carboxylic acid chloride, carboxylic acid ester of carboxylic acid anhydride, the method will encounter obstacles. Therefore, this method has the disadvantage that a special expedient is incorporated therein such as the use of a strong dehydrating agent in the case of a water soluble carboxylic acid sample. Method (2) is a method in which the acidic property of carboxylic acid is determined, but this method also has the disadvantages that when an acidic substance such as inorganic acid or sulfonic acid coexists with carboxylic acid, the determination of the carboxylic acid is impeded to a degree that the determination becomes impracticable and the determination accuracy varies substantially depending upon the type of carboxylic acid employed. Method (3) is not a method which utilizes a peculiar reaction for carboxylic acid and the determination is greatly impeded when any substance which is easily subject to oxidization coexists with the carboxylic acid. Finally, method (4) has disadvantages substantially the same as those described in connection with method (2) hereinabove.

Therefore, the object of the present invention is to provide a method for determining carboxylic acid which can effectively eliminate the above-mentioned disadvantages inherent in the prior art determination methods for carboxylic acid.

A further object of the present invention is to provide a method for determining carboxylic acid in a simple and precise manner.

Another object of the present invention is to provide a method for determining carboxylic acid in which only carboxylic acid is selectively determined by directly forming hydroxamic acid from carboxylic acid and hydroxylammonium salt whether any substance which is easily subjected to oxidization coexists with the carboxylic acid or not.

As one aspect of the present invention, there is provided a method for determining carboxylic acid which comprises the steps of causing a sample of carboxylic acid to react with hydroxylammonium salt in the presence of carbodiimide to form hydroxamic acid and then causing the thus formed hydroxamic acid to react with a ferric compound to form ferric hydroxamate.

DETAILED DESCRIPTION OF THE INVENTION

According to the present invention, a sample containing carboxylic acid (the same will be referred to as "carboxylic acid sample" hereinafter) is reacted with a high concentration solution of hydroxylammonium salt (hydroxylamine perchlorate or hydroxylamine nitrate, for example) dissolved in an organic acid in the presence of a solution of carbodiimide as a coupling reagent for forming an acid amine coupling (1,3-dicyclohexylcarbodiimide or 1-ethyl-3-(3'-dimethylaminopropyl)carbodiimide or salts thereof, for example) dissolved in an organic solvent to directly form hydroxamic acid, then the thus formed hydroxamine acid is merely added to a solution of a ferric compound (ferric chloride or ferric perchloride, for example) dissolved in an organic solvent to form ferric hydroxamate and finally, the color development of the ferric hydroxamate whose pH has been adjusted is determined or the absorptivity of the hydroxamate is determined.

Organic solvents employed as solvents for hydroxylammonium salt in the present invention include one or more of alcohols, ethers, esters, halogenated hydrocarbons, aromatic heterocyclic compounds or mixtures thereof. The organic solvents are allowed to contain water in any amount which will not impede the reaction stages in the determination method of the present invention.

It is convenient in handling hydroxylammonium salt in the organic solvent at a concentration on the order of 1 mol for preservation, but the salt may be in other concentrations in excess or below 1 mol. The concentration of hydroxylammonium salt may be adjusted to a suitable value depending upon the nature of the practical application. In the determination method of the invention, the samples and reagents are not necessarily in solution and may be employed as they are without solvents provided that they are employed under suitable reaction conditions.

The yield of hydroxamic acid by the determination method of the present invention is highest when the method is carried out under the following conditions:

| | |
|---|---|
| Reaction temperature | 40°C – 70°C |
| Reaction time | 5 min. – 30 min. |

-continued

| | |
|---|---|
| Concentration of carbodiimide at the time of reaction | 0.05 mol – 0.5 mol |
| Water content at the time of reaction | 0 – 20% |
| Mol ratio of carbodiimide to hydroxylammonium salt | 1 : 1.0 – 1 : 1.14 |
| Concentration of hydrogen ion | 2.0 – 7.0 (pH) |

BRIEF DESCRIPTION OF THE DRAWING

The sole FIGURE of the accompanying drawing is a flow sheet showing a representative liquid phase flow system in which the determination method of the invention is carried out.

Description will be now made of one example of the determination method of the invention in which the reaction of carboxylic acid is utilized. In this Figure, reference numeral 1 denotes a carboxylic acid sample supply source from which a carboxylic acid sample in a liquid phase obtainable from a carboxylic source or an effluent from a column chromatography (carboxylic acid concentration of $1 \times 10^{-4} - 1 \times 10^{-2}$ mol concentration) is fed to a conduit 5 at the flow rate of 0.2 ml/min. The liquid sample will be referred to as first liquid and may comprise carboxylic acid alone or may be a mixture of carboxylic acid with another substance. Reference numeral 2 denotes a hydroxylammonium salt solution source from which hydroxylammonium salt solution (0.2 mol solution) is fed to the conduit 5 at the flow rate of 0.55 ml/min and this solution will be referred to as "second liquid". The first and second liquids are mixed together in the conduit 5 to provide a mixture solution. The mixture solution preferably has the pH value range of 3–6. In order to attain this pH value range, the pH values of the first and second liquids may be adjusted prior to their mixing or the pH value of the mixture solution may be adjusted after the liquids have been mixed together. In either case, the pH value adjustment may be effected by adding a pH adjusting liquid (caustic alkali solution or tertiary amine solution) to the individual liquids or mixture liquid.

In order to cause the first and second liquids to react with each other, a coupling reagent solution such as carbodiimide (0.2 mol solution) is fed to the conduit 5 from a coupling reagent solution source 3 at the flow rate of 0.5 ml/min (the reagent solution will be referred to as "third liquid") to allow the third liquid to mix with the mixture liquid comprising the first and second liquids. The resultant mixture is then conducted to a constant temperature tank 6 which is in communication with the conduit 5. In order to accelerate the mixing of the first, second and third liquids of the resultant mixture, the constant temperature tank 6 is maintained at the temperature range of 40°–70°C and in this tank, the carboxylic acid and hydroxylammonium salt are reacted with each other in the presence of carbodiimide to form hydroxamic acid. In the present invention, the mixture liquid comprising the first, second and third liquids preferably has a water content below 20%. For the purpose, the water contents in, concentrations and feeding rates of the first, second and third liquids are suitably related to each other and the reaction is carried out under the above-mentioned reaction conditions. Furthermore, from an organic solvent supply source 4, an organic solvent of ferric compound (0.02 mol solution) (the solvent will be referred to as "fourth liquid") is fed to the conduit 5 at the flow rate of 0.3 ml/min to mix with the mixture so as convert the hydroxamic acid to ferric hydroxamate which develops a red color. The final mixture liquid comprising the first, second, third and fourth liquids is required to be sufficiently acidic. For the purpose, a suitable pH adjusting liquid is fed to the conduit 5 to the mixture liquid of the first, second and third liquids prior to the mixing of the fourth liquid thereto or the pH adjusting liquid is previously added to the fourth liquid.

After the mixing of the fourth liquid to the mixture of the first, second and third liquids, the four-liquid mixture is passed to a fluid color meter 7 provided with a fluid cell where the color developed in the ferric hydroxamate is determined. The highest sensitivity is obtained within a determination wave length range of 480–550 $\mu$. If necessary or desired, the developed color may be recorded by an automatic recording device 8 associated with the fluid colormeter. In the sole FIGURE, reference numerals 9, 10, 11 and 12 denote coiled conduits, respectively, and reference numeral 13 denotes a change-over valve.

The hydroxylammonium salt dissolved in an organic solvent employed in the present invention has useful applications such as (a) a spray reagent for qualitative and quantitative determination of the above-mentioned sample by film chromatography or paper chromatography, (b) a reagent for quantitative and qualitative determination of the above-mentioned sample or a solution of solid containing such a sample and (c) an automatic analytic reagent for the above-mentioned sample in a liquid phase fluid.

The present invention will now be more particularly described by way of specific examples of the invention which show the invention for illustration purpose only, but not for limiting the same in any way.

EXAMPLE 1

A ethanol solution of 1,3-dicyclohexylcarbodiimide was sprayed onto spots of a sample on a paper chromatogram or film chromatogram. Then, a solution containing 3.7 g. of hydroxylamine perchloride and 1.3 g. of ferric perchlorate in 100 ml. of ethanol containing 0.01 mol of perchlorate was sprayed onto the spots to thereby detect the carboxylic acid as clearly red spots.

EXAMPLE 2

0.275 mol of hydroxylamine perchloride in 1.0 ml. of ethanol and 0.5 mol of 1,3-dicyclohexylcarbodiimide in 0.5 ml. of ethanol were added to a carboxylic acid sample in 1.0 ml. of ethanol and the materials were reacted with each other at 60°C for 30 minutes to provide hydroxamic acid. Thereafter, 1.0 ml of ethanol containing 2.0 mols of perchloride having ferric perchloride in the concentration of 0.01 mol was added to the hydroxamic acid to provide ferric hydroxamate. The carboxylic acid in the ferric hydroxamate could be precisely quantitatively determined by detecting the color development of the ferric hydroxamate or by determining the absorptivity of the ferric hydroxamate with a suitably selected wave length. The procedure of this example is suitable for determining carboxylic acid in amounts below $5.0 \times 10^{-6}$ mols.

EXAMPLE 3

3.0 ml. of ethanol solution containing 0.1 mol of hydroxylamine perchlorate and 0.5 ml. of ethanol solution containing 0.5 mol of 1,3-dicyclohexylcarbodiimide were added to 0.5 mol of an aqueous carboxylic acid sample and the materials were reacted with each other at 50°C for 30 minutes to provide ferric hydroxamate. 1.0 ml. of ethanol solution containing 0.5 mol of perchlorate having ferric perchlorate in the concentration of 0.02 mol was added to the thus obtained hydroxamate acid to develop the red color. By determining the absorptivity of the product with a wave length of 500–550 $\mu$, the carboxylic acid in the product could be more precisely quantitatively determined than by the conventional methods. The procedure of this example is suitable for carboxylic acid in amounts below $5.0 \times 10^{-6}$ mols.

EXAMPLE 4

A carboxylic acid effluent from a chromatography column or a sampled carboxylic acid which comprised 0.2 mol of hydrochloric acid in which carboxylic acid was dissolved in the concentration range of $1 \times 10^{-4}$ – $1 \times 10^{-2}$ was pumped to a conduit connected to a constant flow rate pump at the flow rate of 0.2 ml/min. A mixture solution comprising an ethanol solution containing 0.2 mol of hydroxylamine perchlorate and an ethanol solution containing 0.06 mol of triethyleneamine in the ratio of 1:1.2 was pumped to the conduit at the flow rate of 1.0 ml/min by a constant flow rate pump and then, an ethanol solution containing 0.2 mol of 1,3-dicyclohexylcarbodiimide was pumped to the conduit at the rate of 0.5 ml/min by a constant flow rate pump. The solutions were passed to and through the constant temperature tank maintained at 60°C for 5 minutes. Thereafter, a perchlorate ethanol solution containing ferric perchlorate (a solution of 0.5 mol of ferric perchlorate dissolved in an ethanol having perchlorate in the concentration of 0.5 mol) was pumped to the constant temperature tank at the flow rate of 0.3 ml/min where the solutions were then reacted with each other to form ferric hydroxamate. The color developed in the ferric hydroxamate was determined by a fluid colormeter to find the absorptivity of 525 $\mu$. By the procedure, carboxylic acid could be more precisely determined by the conventional methods.

As clear from the foregoing, according to the present invention, the carboxylic acid can be quite effectively determined in the presence of the other coexisting acidic components in products containing carboxylic acid without being subjected to any impedance by such acidic components. Furthermore, the method of the present invention is quite advantageously applied to foodstuff component samples and industrial product samples which are usually handled in great quantity, or clinical medicine samples which are usually handled in quite small quantities in automatically and quantitatively determining the amount of carboxylic acid contained in the samples.

While only several examples of the invention have been described in detail, it will be understood that the same are for illustration purpose only and not to be taken as a definition of the invention, reference being had for that purpose to the appended claims.

What is claimed is:

1. In a method for determining the presence or amount of carboxylic acid in a sample by mixing the sample with a hydroxylamine whereby any carboxylic acid in the sample will react with the hydroxylamine to form hydroxamic acid, and thereafter determining the presence of hydroxamic acid in the mixture, the improvement which comprises mixing the sample with hydroxylamine and a carbodiimide.

2. The method of claim 1 wherein the presence of hydroxamic acid is determined by adding a ferric compound to the mixture whereby any hydroxamic acid present will react with the ferric compound to form ferric hydroxamate.

3. The method of claim 1 wherein the carbodiimide is employed at a concentration of 0.05–0.5 mol, the mol ratio of the carbodiimide to the hydroxylamine is 1:1 to 1:1.14, and wherein the mixing of the sample, hydroxylamine and carbodiimide is carried out for 5–30 minutes at a temperature of 40°–70°C. and a pH of 2–7.

4. The method of claim 3 wherein the pH is 3–6 and the mixture contains up to 20% water.

5. The method of claim 1 wherein the hydroxylamine is hydroxylamine perchlorate or hydroxylamine nitrate and wherein the carbodiimide is a member of the group consisting of 1,3-dicyclohexylcarbodiimide, 1-ethyl-3-(3'-dimethylaminopropyl)carbodiimide and the salts thereof.

6. The method of claim 5 wherein the presence of hydroxamic acid is determined by mixing ferric chloride or ferric perchloride with the mixture whereby any hydroxamic acid present will react with the ferric compound to form ferric hydroxamate.

7. The method of claim 6 wherein the amount of ferric hydroxamate formed is determined by colorimetry.

8. The method of claim 6 wherein the mixing of the sample, hydroxylamine and carbodiimide is carried out in a first zone, the addition of the ferric compound to the resulting mixture is carried out in a second zone, and wherein the amount of ferric hydroxamate formed is determined by colorimetry in a third zone.

9. The method of claim 1 wherein the mixing of the sample, hydroxyl amine and carbodiimide is carried out in a first zone and the presence of hydroxamic acid is determined in a second zone.

10. The method of claim 1 wherein said sample is a chromatography effluent.

* * * * *